United States Patent
Gleckler et al.

(10) Patent No.: US 8,477,039 B2
(45) Date of Patent: Jul. 2, 2013

(54) PROVIDING INFORMATION RELATED TO THE POSTURE MODE OF A USER APPLYING PRESSURE TO A SEAT COMPONENT

(75) Inventors: Anthony D. Gleckler, Tucson, AZ (US); Vi-Vie Ng, Kuala Lumpur (MY); Daniel Whitworth, Virginia Beach, VA (US); Kyle Cotner, Hannover (DE); Timothy Ryan Hall, San Diego, CA (US)

(73) Assignee: Geoat, Inc., Tucson, AZ (US)

( * ) Notice: Subject to any disclaimer, the term of this patent is extended or adjusted under 35 U.S.C. 154(b) by 962 days.

(21) Appl. No.: 12/123,239

(22) Filed: May 19, 2008

(65) Prior Publication Data

US 2009/0058661 A1 Mar. 5, 2009

Related U.S. Application Data

(60) Provisional application No. 60/939,025, filed on May 18, 2007.

(51) Int. Cl.
| | |
|---|---|
| *G08B 23/00* | (2006.01) |
| *G08B 25/00* | (2006.01) |
| *G08B 21/00* | (2006.01) |
| *F01N 1/08* | (2006.01) |

(52) U.S. Cl.
USPC ........ 340/573.7; 340/524; 340/666; 340/667; 181/273

(58) Field of Classification Search
USPC ............................................ 340/666; 177/144
See application file for complete search history.

(56) References Cited

U.S. PATENT DOCUMENTS

| | | | |
|---|---|---|---|
| 6,272,936 B1 | 8/2001 | Oreper et al. | |
| 6,348,663 B1* | 2/2002 | Schoos et al. | 177/144 |
| 6,689,974 B2* | 2/2004 | Guillot | 200/85 A |
| 7,046,158 B2* | 5/2006 | Saunders et al. | 340/666 |
| 7,109,872 B2* | 9/2006 | Balaban et al. | 340/573.7 |
| 2003/0222767 A1* | 12/2003 | Patterson et al. | 340/425.5 |
| 2004/0207530 A1* | 10/2004 | Nielsen | 340/604 |
| 2007/0068720 A1* | 3/2007 | Fischer et al. | 180/273 |
| 2007/0106475 A1* | 5/2007 | Kondoh | 701/301 |

OTHER PUBLICATIONS

Transmittal of Supplemental Information Disclosure Statement.

\* cited by examiner

*Primary Examiner* — Nabil H. Syed
*Assistant Examiner* — Pameshanand Mahase

(57) ABSTRACT

A system for producing information about the posture of a user applying pressure to a seat component is provided. A sensor structure with array of sensors is connected with the seat component, with the sensors in a predetermined pattern configured to provide output signals related to predetermined posture modes of the user applying pressure to the seat component. The output of the sensors in circuit communication with a processor to provide signals to the processor related to predetermined posture modes of the user applying pressure to the seat component, and the processor provides output related to the predetermined posture modes of the user applying pressure to the seat component.

8 Claims, 11 Drawing Sheets

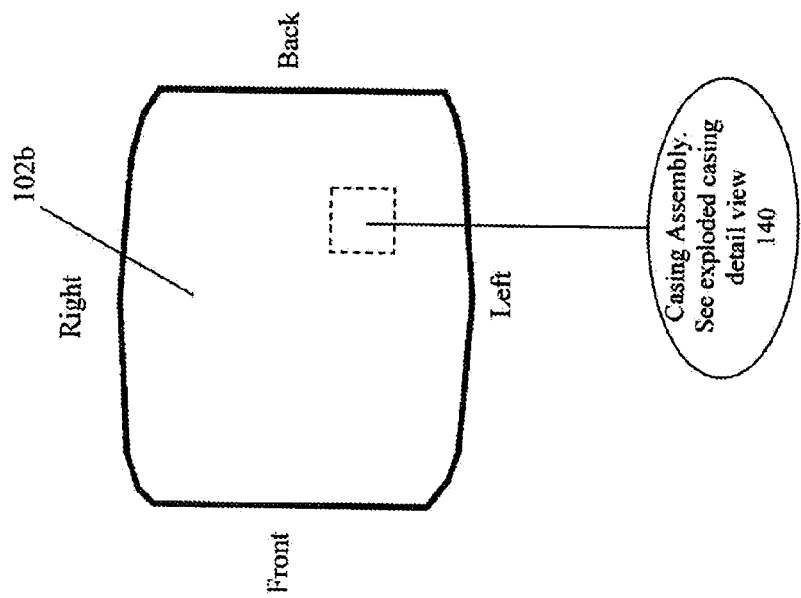
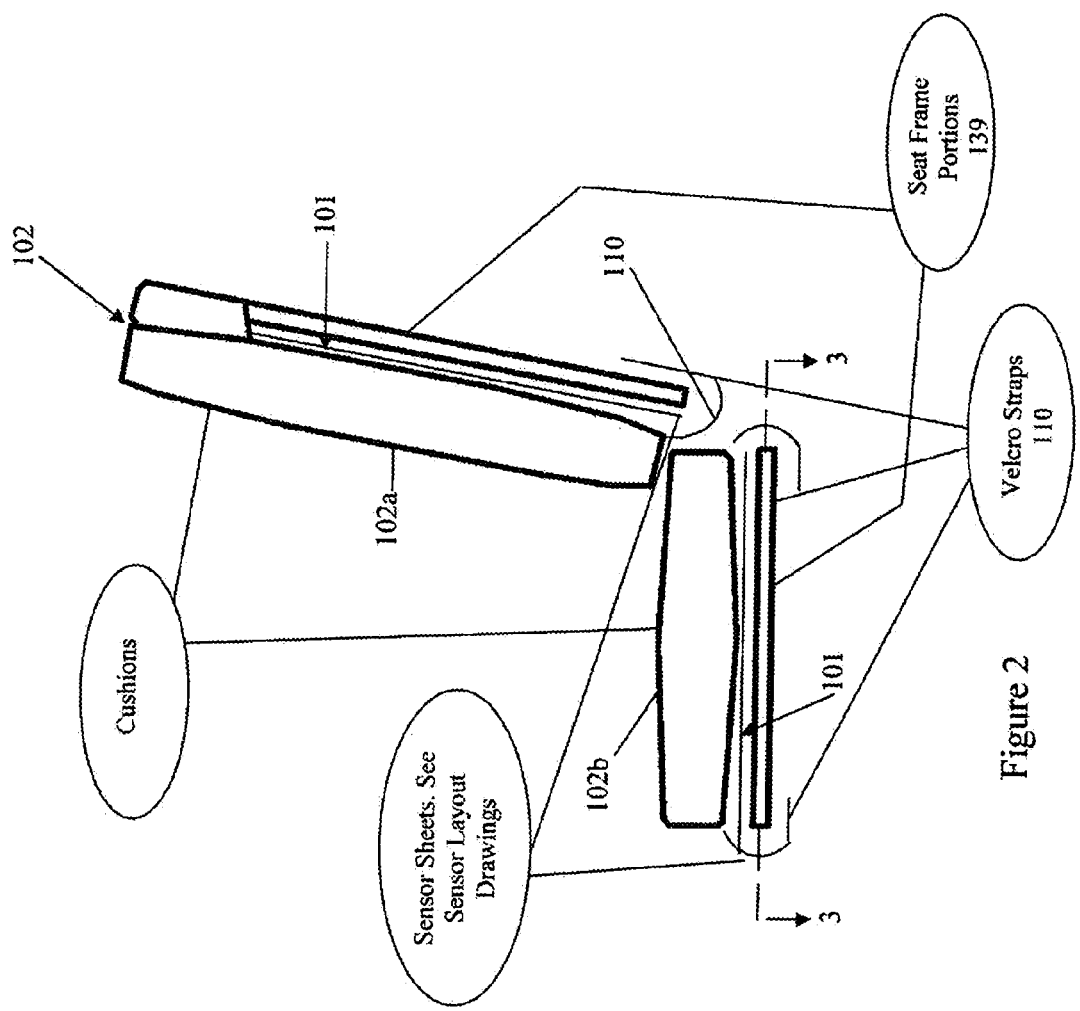
Figure 3
Figure 2

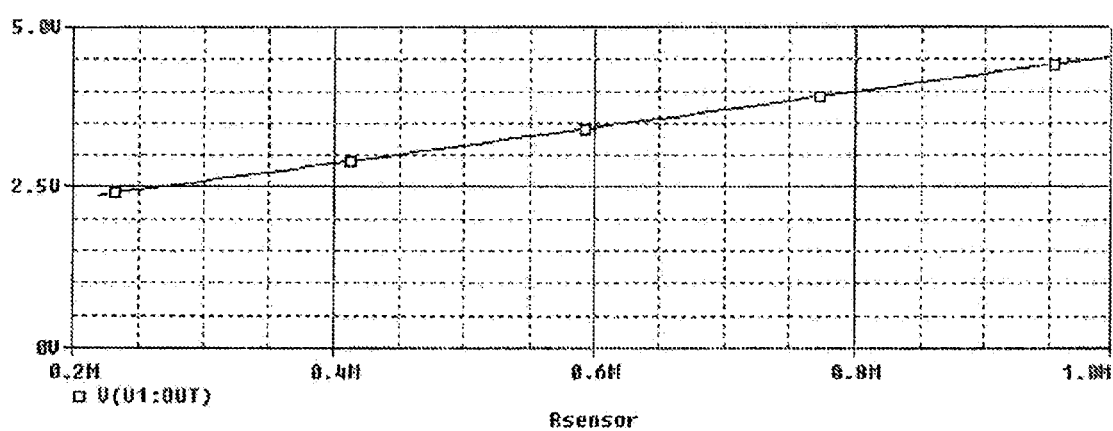
Figure 14: Vout vs. Rsensor

PROVIDING INFORMATION RELATED TO THE POSTURE MODE OF A USER APPLYING PRESSURE TO A SEAT COMPONENT

RELATED APPLICATION/CLAIM OF PRIORITY

This application is related to and claims priority from provisional application Ser. No. 60/939,025, filed May 18, 2007, which provisional application is incorporated by reference herein.

BACKGROUND

A vast majority of the corporate world spends greater than six hours a day sitting at a desk. These employees can spend the greater part of their day sitting in positions of bad posture without even realizing it. By sitting in these positions for such long periods of time, they are inviting unwanted back problems. This could result in poor performance, decreased productivity, and ultimately absence from work.

Although ergonomic products do exist, their passive nature leaves the user uncertain as to whether or not they are using the product correctly. An ergonomic chair, for example, may be perfectly built to correct one's posture while sitting. However, without proper instructions or feedback, the user will become unaware of the incorrectness of their sitting position. Most human beings lack the refined sensory awareness of the joints or muscles to be continually aware of their posture while engrossed in their work. This unintentional indifference could cause the user to sit in a position that does not contribute towards good posture. The ineffective use of the ergonomic chair could result in health problems among users, namely back problems, carpal tunnel syndrome, etc.

SUMMARY OF THE PRESENT INVENTION

The present invention is designed to address the foregoing needs. In a basic aspect, the present invention provides a system for producing information about the posture of a user applying pressure to a seat component, comprising
a. sensor structure with an array of sensors connected with the seat component, at predetermined locations and in a predetermined pattern configured to provide output signals related to predetermined posture modes of the user applying pressure to the seat component,
b. the output of the sensors in circuit communication with a processor to provide signals to the processor related to predetermined posture modes of the user applying pressure to the seat component, and
c. the processor providing output related to the predetermined posture modes of the user applying pressure to the seat component.

In a system according to the present invention, the processor has an output that is in circuit communication with a posture mode indicator that provides an indication of the posture mode of the user applying pressure to the seat component. The posture mode indicator may comprise any or all of the following: a visual output, an audio output, a vibration output, or an output that is directed to a data file.

In a preferred form of the sensor structure of the present invention, the predetermined pattern of the sensors is designed to provide output related to any or all of the following posture modes: correct posture, hunch, slumping, leaning forward, leaning left or right, diagonal left or right, and slouching. Each sensor comprises a pressure pad in force transmitting relation with a predetermined location on the seat component, each sensor configured to receive a load applied to the predetermined portion of the seat component such that the array of sensors provides output related to any or all of the following posture modes: correct posture, hunch, slumping, leaning forward, leaning left or right, diagonal left or right, and slouching. In a currently more preferred from, each sensor includes a force transmitting member connected to and extending between the pressure pad and a predetermined location on the seat component, the force transmitting member formed of elastically deformable material and configured to spread a load applied to the predetermined portion of the component and to transmit the load substantially across the pressure pad, such that the sensor provides output related to any or all of the following posture modes: correct posture, hunch, slumping, leaning forward, leaning left or right, diagonal left or right, and slouching. Also, the pressure pad of each sensor rests on one side of an elastically deformable support member and the other side of the elastically deformable support member is connected to a base member that is used to connect the sensor to a support.

Still further, in the preferred form of sensor structure of the present invention, the array of sensors is prepackaged so it can be delivered to a user in the predetermined format. The array of sensors include pressure pad sensors (e.g. formed of pressure sensing ink) connected to and disposed between a pair of flexible sheets, in a predetermined pattern, to form a preformed sensor array. At least one of the sheets has sensor locating markings thereon (where the pressure pads are located), to enable elastically deformable members (referred to as pucks) through which force is applied to the sensors to be properly located relative to the pressure pad sensors during assembly of a seating component with the sensor array. Additionally, the pair of flexible sheets has a wire layout that enables the array of pressure pad sensors to be connected to a terminal via the wire layout.

Additionally, in the currently preferred form of the system of the present invention, the seat component comprises a cushion and the sensor structure (e.g. the flexible sheets, the pressure pad sensor, the elastically deformable members) are configured such that the sensor structure can be effectively connected between the seat cushion and the support for the seat cushion (e.g. the relatively hard frame of a chair) in a manner that minimizes the likelihood of a false signal being applied to the sensor structure, while enabling the sensor structure to provide signals to the processor that are related to the predetermined pressure modes. Also, the various posture modes can be sensed with a relatively sparse array of sensors, with sensor structure located between a seat cushion and the relatively hard chair frame portion, the sensor structure can be produced as an OEM product that can be incorporated into a chair in a manner that does not materially affect the basic aesthetics and comfort of the chair.

A system according to the present invention can also have a number of optional features. For example, the system can include a calibration mechanism that enables the seat component to be calibrated to a particular user's weight and size. The system can be configured such that the output of the processor can have a plurality of formats related to the predetermined posture modes, and a user can select the format of the output. Moreover, the system can be configured to provide an alert when an operating condition of the system may affect the processor output in an undesirable way. Also, the system can be configured such that the output of the processor has at least one form that informs the user that the system is reacting correctly to the user's position on the seat component.

When the principles of the present invention are used in an ergonomic chair the user can be notified of their sitting position via a graphical desktop computer display. The display can aid the user by offering a reminder of sitting position so that the user can make the necessary adjustments to ensure better posture. By giving posture feedback to the user, an ergonomic chair incorporating the principles of the present invention will initiate corrective action, and possibly prevent unnecessary health problems.

These and other features of the present invention will become further apparent from the following detailed description and the accompanying drawings and exhibits.

BRIEF DESCRIPTION OF THE DRAWINGS AND EXHIBITS

FIG. 2 is a schematic illustration of a seat (also referred to as a chair) in a system according to the principles of the present invention;

FIG. 3 is a sectional view of the chair show in FIG. 1, taken from the direction 3-3, and showing a location for the casing assembly shown in FIG. 12;

Figure 5:
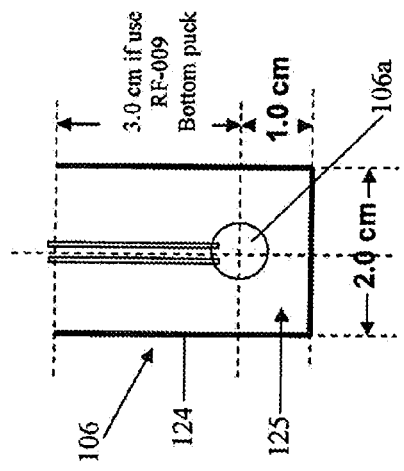
Figure 4:
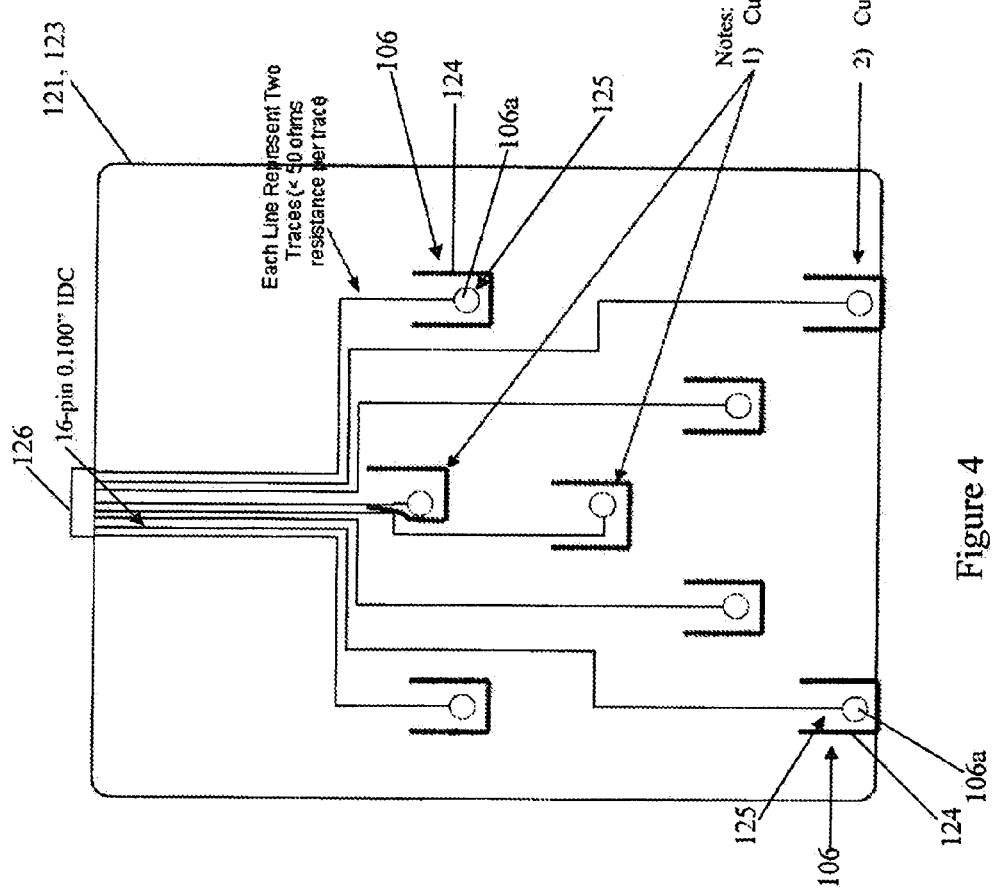
FIG. 4 is a schematic illustration of a sensor structure with a sensor array and a pair of flexible sheets, with the sensor array in an exemplary sensor pattern that can be used with either a chair seat or a chair back, according to the principles of the present invention.
Figure 6:
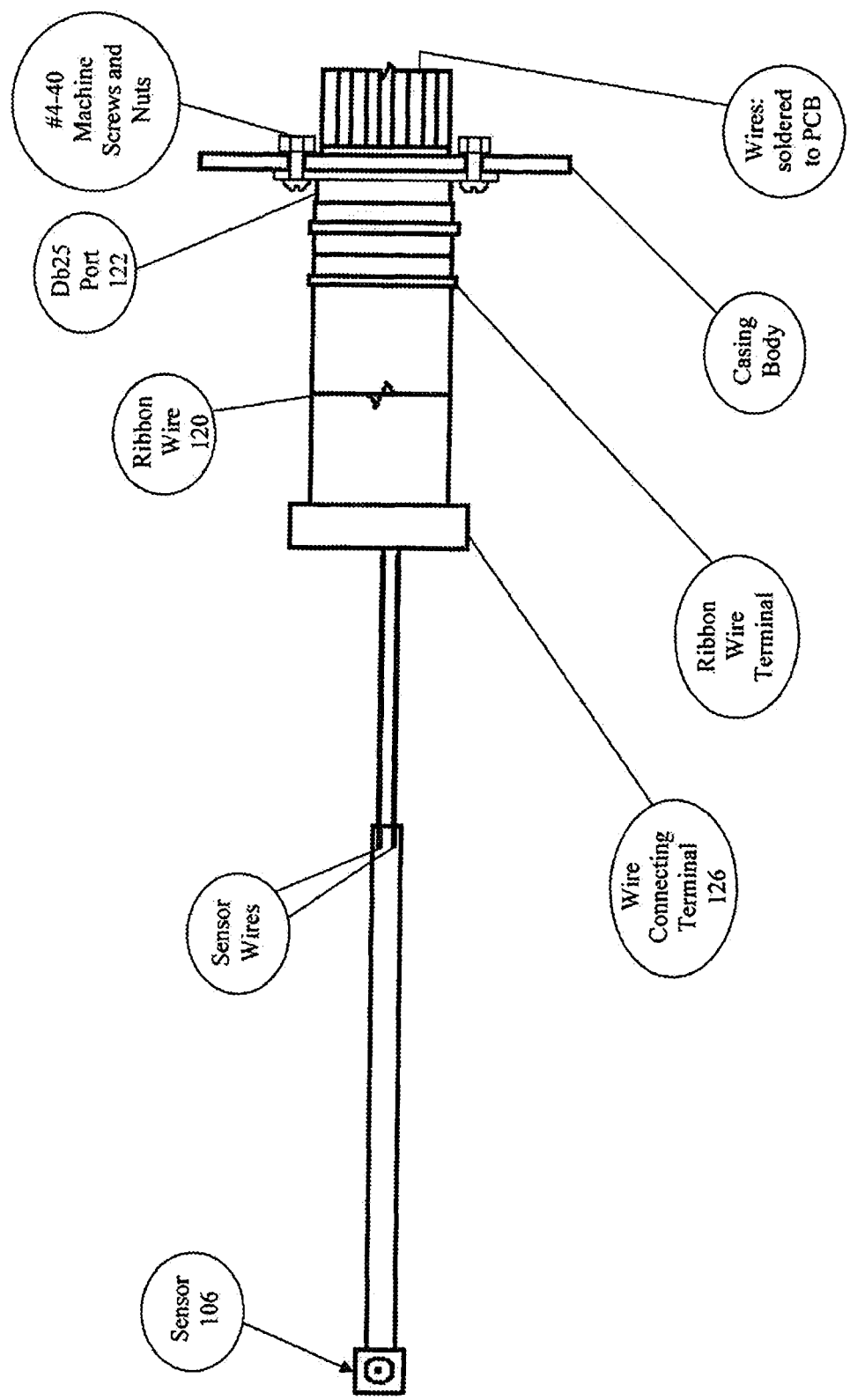
Figure 7:
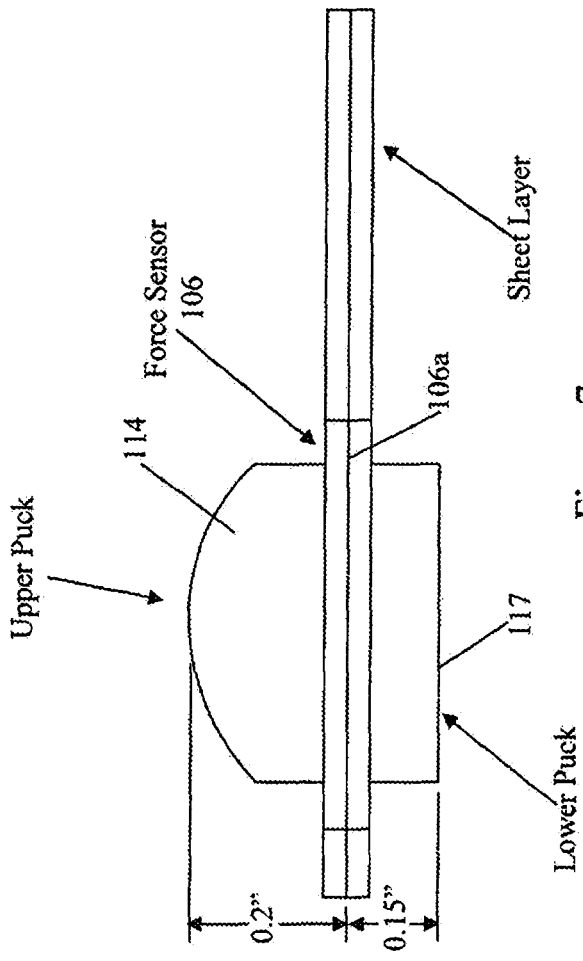
Figure 8:
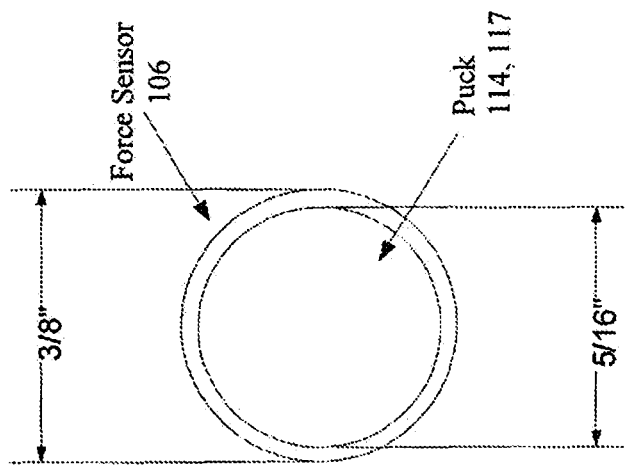
Figure 9:
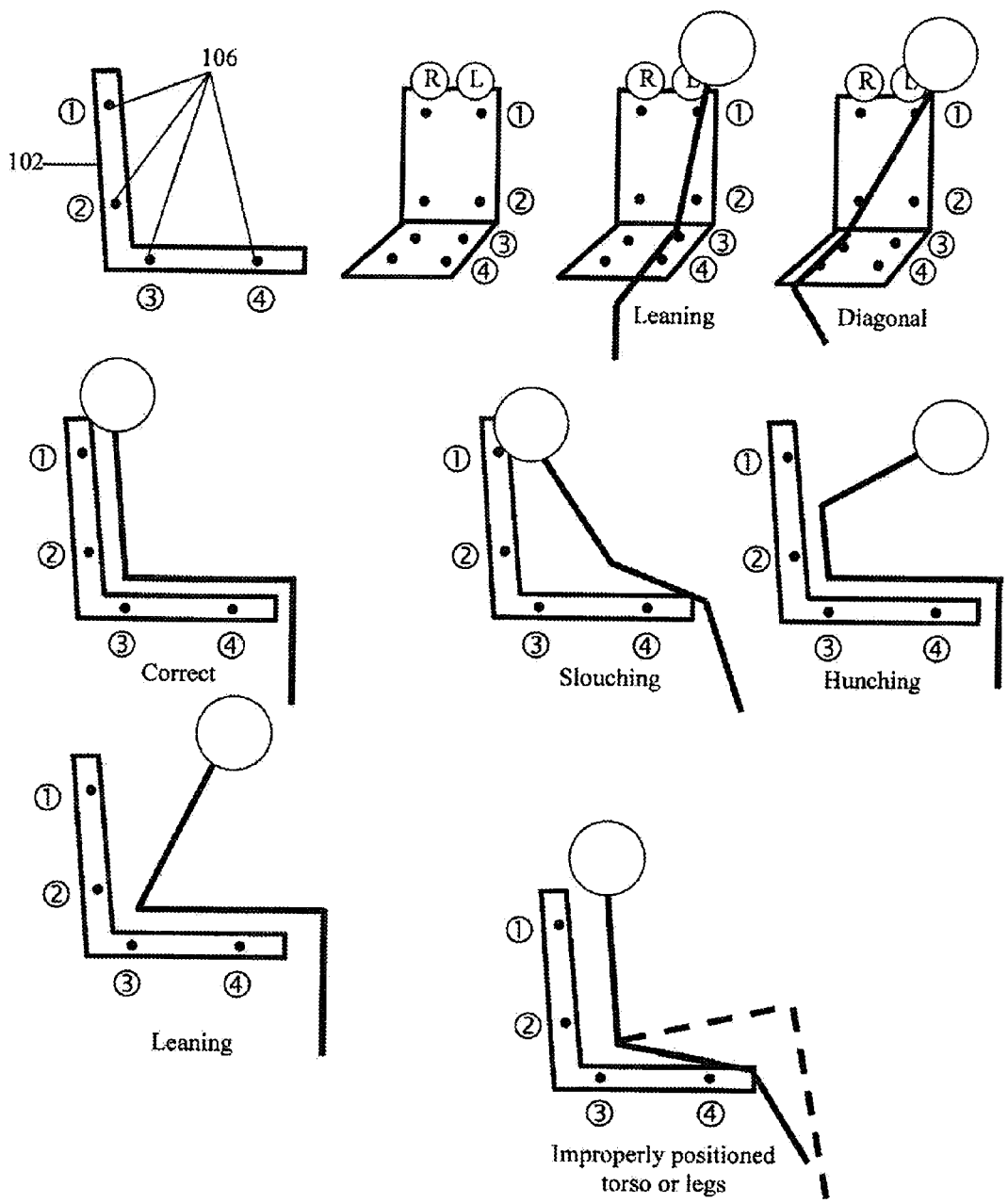
Figure 10:
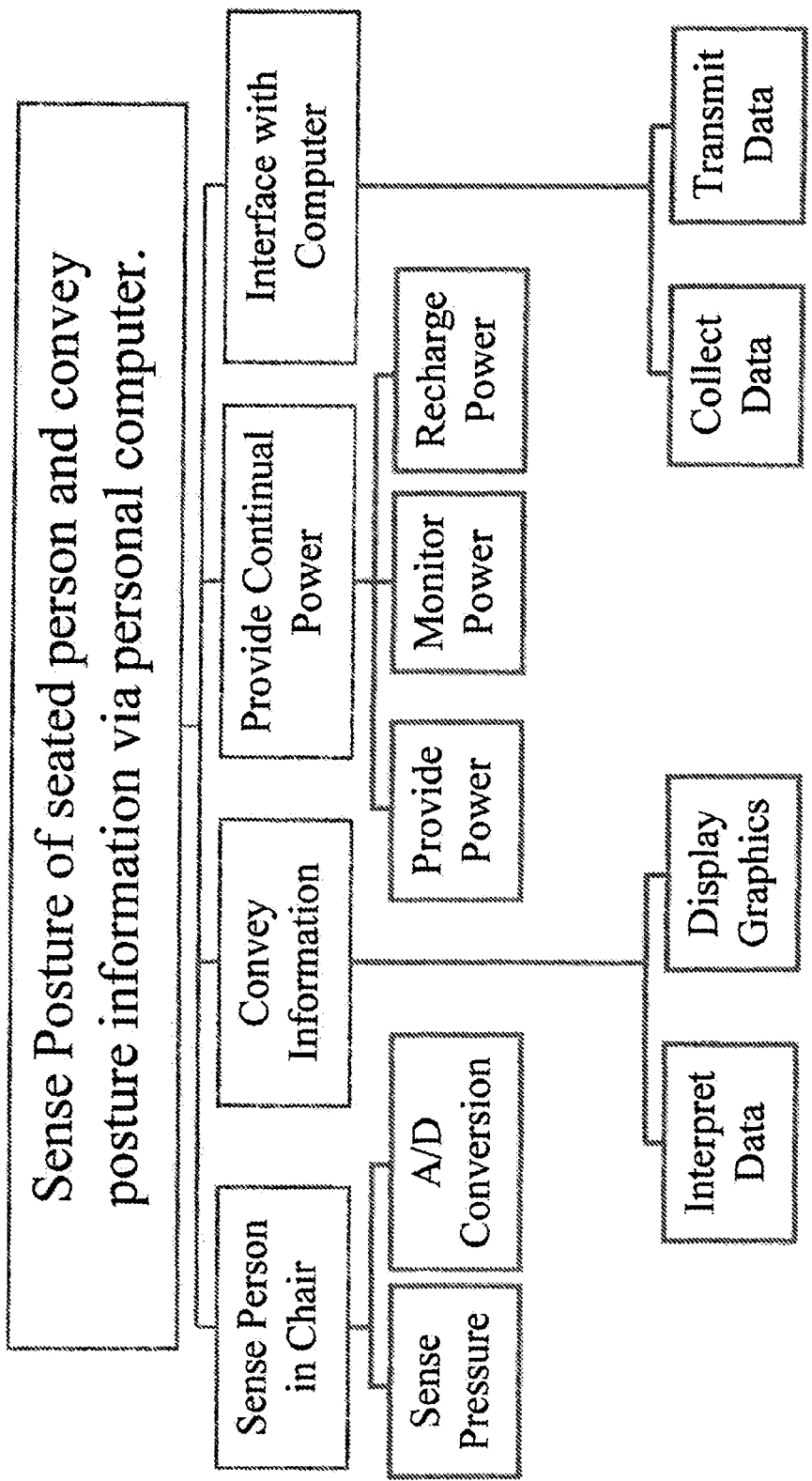
Figure 11:
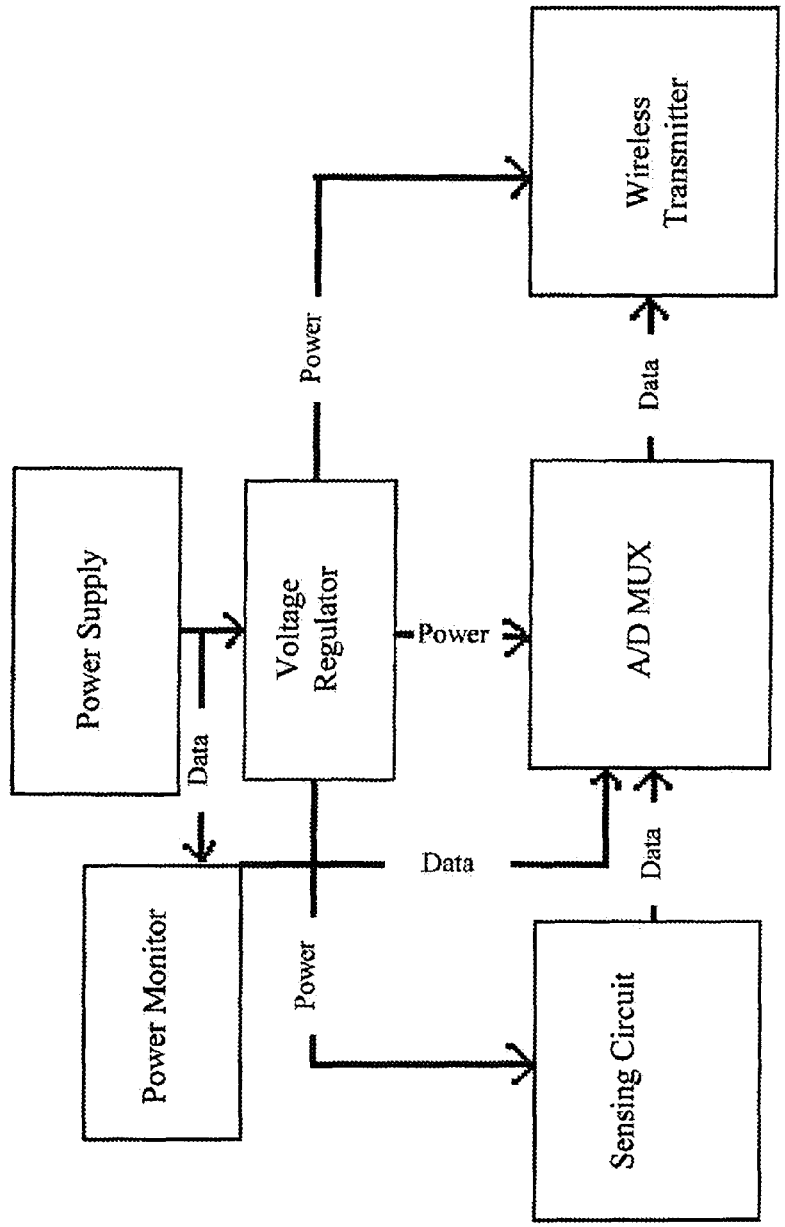
Figure 12:
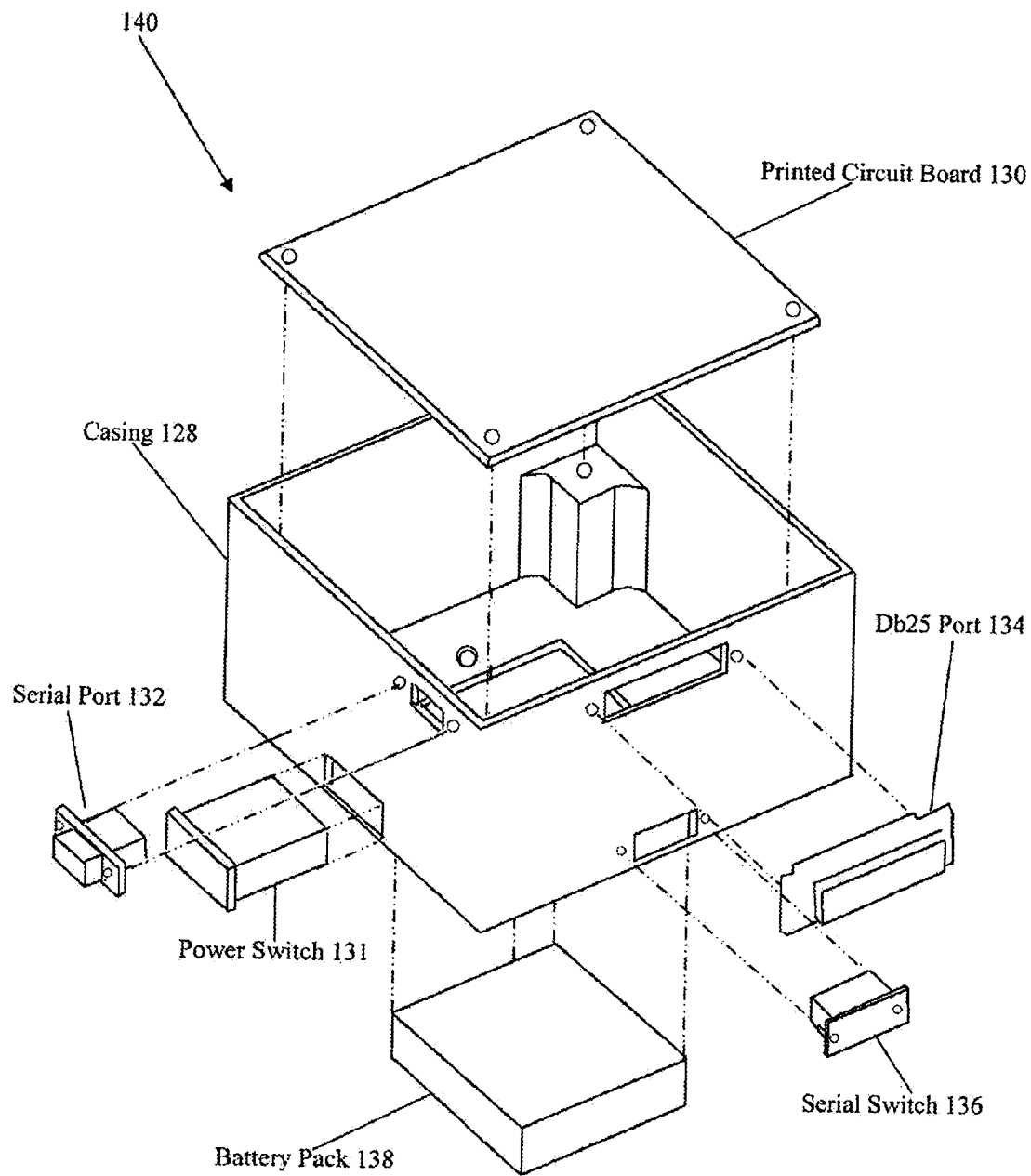
Figure 13:
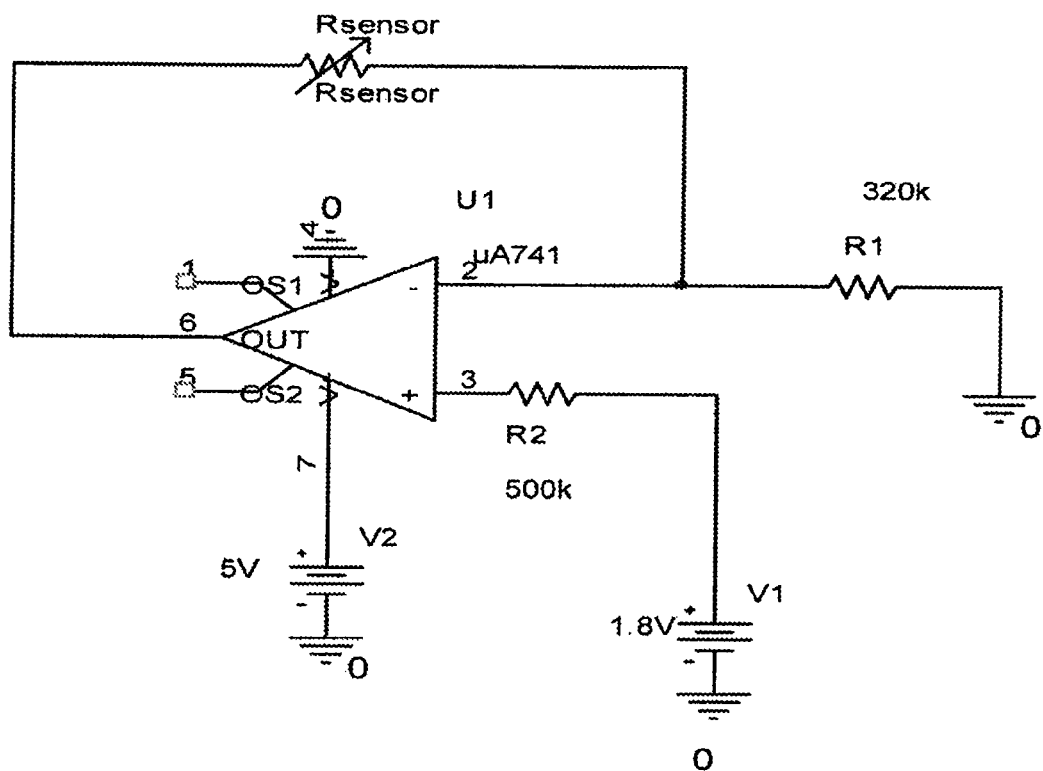

FIG. 5 is a schematic illustration of one of the sensors in the sensor array of FIG. 4, with some exemplary dimensions shown thereon, and further showing a pattern for a cut in the pair of supporting flexible sheets that enables sensor structure according to the present invention to be effectively connected between a seat cushion and the support for the seat cushion in a manner that minimizes the likelihood of a false signal being applied to the sensor structure;

FIG. 6 is a schematic illustration of a sensor, and some of its connecting structure, that can be used in the system of FIGS. 1-5;

FIG. 7 is a side view of the sensor head shown in FIG. 6, with some exemplary dimensions shown thereon;

FIG. 8 is top view of the sensor head shown in FIG. 6, with some exemplary dimensions shown thereon;

FIG. 9 is a schematic illustration of a sensor array incorporated in a seat, and various posture modes that are sensed and may be displayed, in a system according to the present invention;

FIG. 10 is a schematic illustration of the Functional Operation of a system according to the principles of the present invention;

FIG. 11 is a schematic illustration of a power flow chart for a system according to the present invention;

FIG. 12 is an exploded schematic illustration of a casing assembly for certain of the mechanical components of a system according to the present invention; and FIG. 13 is a circuit diagram of a circuit associated with a sensor, in a system according to the present invention;

FIG. 14 shows a simulated plot of the output voltage vs. the resistance of the sensor.

Figure 1:
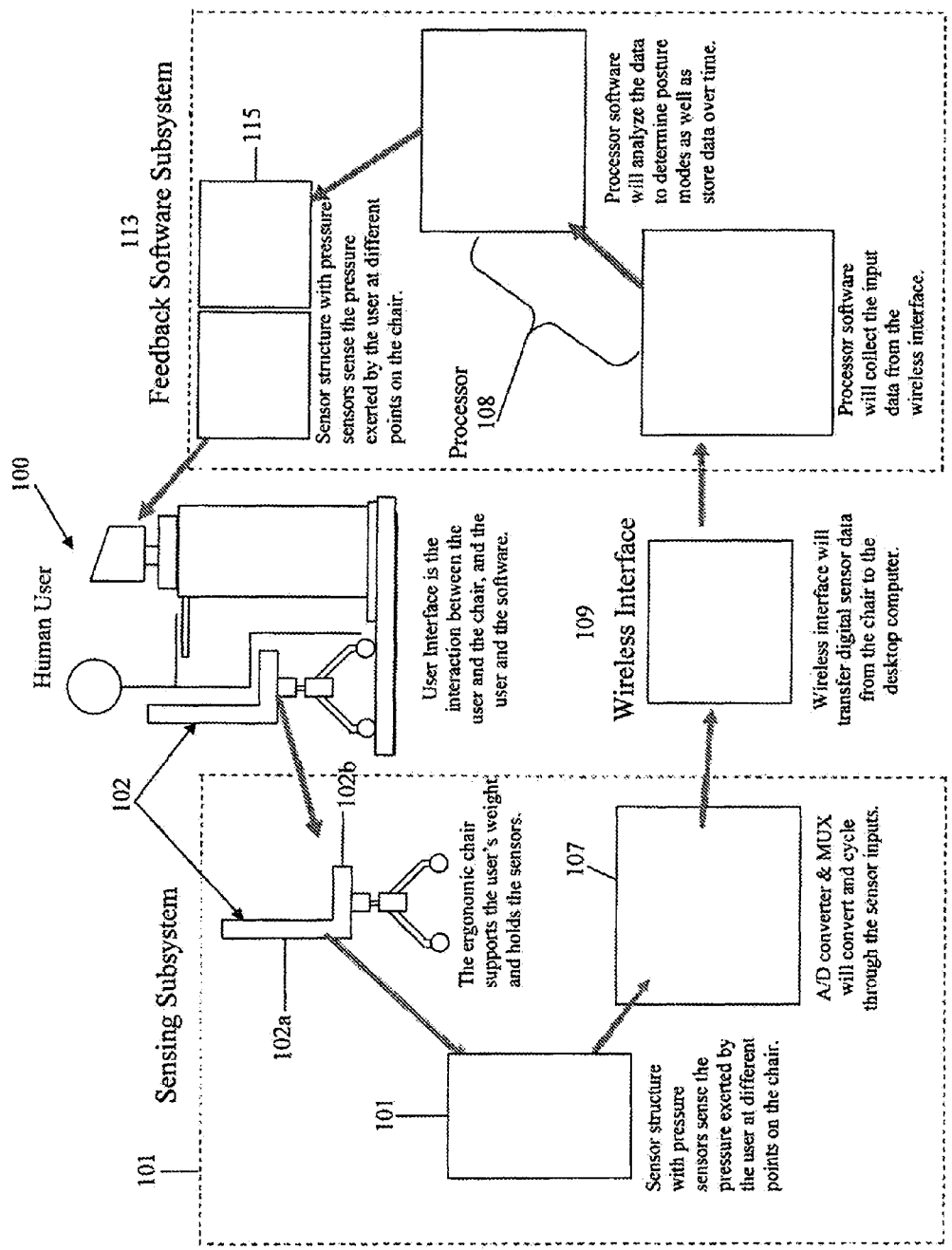
FIG. 1 is a schematic illustration of a system according to the principles of the present invention.

Exhibit A is a figure similar to FIG. 1, and showing some additional details of the system of FIG. 1.

Exhibit B shows schematics for the electronics of a PCB used to construct a prototype of a system according to the principles of the present invention.

DETAILED DESCRIPTION

As described above, the present invention provides a system for producing information about the posture of a user applying pressure to a seat component. The principles of the present invention are described below in connection with a chair that has seat components such as a seat cushion and a back cushion for supporting a user. From that description, the manner in which the principles of the present invention can be used with various forms of seat components will be apparent to those in the art.

DEFINITIONS

In this application, sensors being in "circuit communication" with a processor means any means by which the sensors transmit data to the processor, including wire communications, wireless communications, etc. Also, a "seat component" can be a seat, a back or an arm rest portion of a chair, which may have e.g. a "cushion" that is a structure that includes at least a contained compliant mass (e.g. foam) that yields when pressure is applied against it. In addition, a "cushion" can be any or all of a seat cushion or back cushion (either or both of which can be integrally formed into a chair, or designed to be applied to a chair), or a cushion that serves as an armrest of a chair. Still further, a "processor" is any device that can take the input from the sensor(s) and produce an output that is related to the posture of the person applying pressure to the cushion. Furthermore, an "array of sensors" located to produce output related to one or more "posture modes" means a plurality of sensors that are selectively located in relation to a seat component such that they respond to pressure at their selective locations in a manner such that their output can be related to one of a number of predetermined posture positions, as opposed to a large number of sensors disposed over an entire surface to enable the sensors to produce a complete pressure map of a body applying pressure to the surface. Additionally, a sensor structure "connected with a cushion" means that the sensor structure can be directed connected to the cushion, or indirectly connected to the cushion through an intermediate member. It should also be noted that a "pressure pad" is e.g. an area sensor (which can be formed, e.g. of pressure sensitive ink) that is capable of measuring the average force over the area of the sensor—this can be done directly via pressure, or indirectly via force or displacement. Finally, reference to a "sensor structure" is intended to include a subassembly that can be incorporated into a chair, and provides the means by which signals related to the pressure applied to a seat component are produced and transmitted (e.g. a pair of flexible sheets with pressure pads and wiring disposed between the flexible sheets, and elastically deformable members, called "pucks", that may be attached to the exterior of the flexible sheets in force transmitting relationship with the pressure pads).

As shown in FIG. 1 (and Exhibit A) a system 100 is provided for producing information about the posture of a user applying pressure to a seat component, which can be a chair 102 with a back cushion 102a and a seat cushion 102b. The system 100 includes a. A sensor structure 101 which has an array of sensors 106 connected with the seat component, at predetermined locations and in a predetermined pattern (e.g. FIG. 4) configured to provide output signals related to predetermined posture modes of the user applying pressure to the seat component, b. the output of the sensors in circuit communication (e.g. via a wireless interface 109) with a processor 108 to provide signals to the processor related to predetermined posture modes of the user applying pressure to the seat component, and c. the processor providing output (e.g. via a feedback software system 113 with graphics and warning displays 115) related to the predetermined posture modes of the user applying pressure to the seat component.

In a system according to the present invention, the processor 108 has an output that is in circuit communication with a posture mode indicator (e.g. the graphics and warning displays 115) that provides an indication of the posture mode of the user applying pressure to the seat component. The posture mode indicator may comprise any or all of the following: a visual output, an audio output, a vibration output, or an output that is directed to a data file.

In a preferred form of the present invention, the sensor structure 101 with the predetermined pattern of the sensors is designed to provide output related to any or all of the following posture modes: correct posture, hunch, slumping, leaning forward, leaning left or right, diagonal left or right, and slouching (those posture modes are schematically shown in FIG. 9). Each of the sensors can be constructed in accordance with U.S. Pat. No. 6,272,936, issued Aug. 14, 2001, which patent is incorporated by reference herein. Each sensor 106 comprises a pressure pad 106a (which can be e.g. formed by pressure sensitive ink) in force transmitting relation with a predetermined location on the seat component, each sensor 106 configured to receive a load applied to the predetermined portion of the seat component such that the array of sensors provides output related to any or all of the following posture modes: correct posture, hunch, slumping, leaning forward, leaning left or right, diagonal left or right, and slouching. In a currently more preferred from, the structure 101 also includes one or more force transmitting members (labeled pucks 114, 117 in FIGS. 7 and 8) connected to and extending between the pressure pad 106a and a predetermined location on the seat component (e.g. the seat back, the seat base, etc.) Each force transmitting member 114, 117 is formed of elastically deformable material and is configured to spread a load applied to the predetermined portion of the seat component and to transmit the load substantially across the pressure pad of the sensor, such that the array of sensors 106 provides output related to any or all of the following posture modes: correct posture, hunch, slumping, leaning forward, leaning left or right, diagonal left or right, and slouching. More specifically, as can be appreciated from FIG. 9, the pattern of sensors forming part of the sensor structure are predetermined so that depending on the posture with which a person sits on the chair, certain of the sensors will sense pressure from that posture, and other sensor may sense no pressure from that posture. The feedback from all of the sensors (i.e. the composite of which sensors sense pressure and which do not sense pressure) is compared with how the sensors should sense pressure when the posture mode is correct, and how pressure is sensed when a posture mode is incorrect, and that comparison enables the system to provide the output that is related to whether the person is in a correct or incorrect posture mode. Also, as will be further apparent from FIGS. 4 and 9, the various posture modes can be effectively sensed with a sensor structure having a relatively sparse array of sensors, and incorporated into a chair in a manner that is designed not to materially interfere with the aesthetics and comfort of the basic structure of the chair.

The initial implementation of the posture mode measurement consists of using the sensor array to provide an estimate of the Centroid of the weight in both the chair's seat and back. The table below shows how the Centroid motion of the user's weight determines the posture mode.

| Posture mode | User's mass Centroid position in seat of chair | User's mass Centroid position in back of chair |
| --- | --- | --- |
| Normal | Centered* | Centered* |
| Slouch | Forward | Upward |
| Hunch | Centered | Downward |
| Lean right | Right | Right |
| Lean left | Left | Left |
| Diagonal Right | Left | Right |
| Diagonal Left | Right | Left |
| Lean Forward | Forward | Downward (more than hunching) |

*"Centered" means the nominal position of the user when the chair is calibrated with the user in a proper position.

The threshold process for determining when the user has shifted from one mode to the other is an adjustable parameter that is dependent on the chair, the user's size and weight, and the user's tolerance for poor postural positions.

By only operating with this limited set of posture modes, the user's position and posture can be measured with a sparse array of sensor and this can be done through the cushion material of the chair. These are key differentiated features compared to pressure sheets that can map a user's weight directly, but must be placed over the chair, and which do not provide actual posture information.

The sensor structure 101 comprises a pair of flexible sheets 121, 123, with force sensing pressure pads 106a and the wiring patterns shown in FIG. 4 printed on the inside of one or both of the flexible sheets, so that the force sensing pressure pads 106a and wiring patterns are protected by the flexible sheets. In addition, the sensor structure also comprises elastically deformable members 114, 117, referred to as pucks, secured to the opposite exterior sides of the flexible sheets 121, 123 at predetermined locations so that the pucks 114, 117 are aligned with the force sensing pressure pads 106a. In addition, as seen from FIGS. 4 and 5, a pattern of cuts 124 are provided in the flexible sheets 121, 123, in predetermined relation to the pucks and the pressure sensing pads. The cuts 124 are configured to form flexible flap portions of the flexible sheets 121, 123 that enable the flaps 125 and the sensors 106 to flex relative to the rest of the flexible sheets. This feature enables the flexible sheets to conform to the seat component on one side of the flexible sheets, while minimizing the application of tension to the flexible sheets as they are being secured to a seat component (thereby minimizing the likelihood of an incorrect pressure signal resulting from such tension). Thus, if pucks 114, 117 are secured to opposite sides of a pair of flexible sheets (as shown in FIG. 7), the pucks on one side of the pair of sheets 121, 123 can be secured to one part of a seat component (e.g. a seat cushion), and the flexible flaps 125 allow the pucks on the other side of the pair of flexible sheets, and also portions of that other side of the pair of flexible sheets, to be secured to the other seat component (e.g. a relatively hard seat frame portion 139 such as a seat frame back or base) while minimizing application of tension to the flexible sheets that could otherwise cause a force sensing pad to incorrectly sense that tension as a load being applied to the sensor structure.

Still further, in the preferred form of the present invention, the pair of flexible sheets 121, 123 with the array of pressure pad sensors 106a can be prepackaged so it can be delivered to a user in the predetermined format shown in FIGS. 4 and 5 (the cuts 124 can also be preformed in the pair of flexible sheets). The array of pressure pad sensors 106a form the preformed sensor array, and at least one of the pairs of flexible sheets 121, 123 has sensor locating markings thereon (see FIG. 4), or the sheets 121, 123 can be transparent, so that the pressure pad sensors 106a can be seen therethrough, to enable the pucks 114, 117 to be properly located relative to the pressure sensing pads, and to also allow the sensor structure to be properly located relative to a seat component. Additionally, the wire layout provided in the flexible sheets 121, 123 enables the array of sensors 106 to be connected to a terminal 126).

Additionally, in the currently preferred form of the system of the present invention, the seat component 102 a, b, comprises a cushion and the sensor structure 101 is designed to be connected between a seat cushion, e.g. a seat, back or arm rest cushion and a seat frame portion 139 (FIG. 2). Also, the sensor structure 101 is designed so that the array of sensors are located in a predetermined pattern in relation to the cushion, the predetermined pattern being designed such that the array of sensors will provide signals to the processor that are related to the predetermined pressure modes.

A system according to the present invention can also have a number of optional features. For example, the system can include a calibration mechanism that enables the seat component to be calibrated to a particular user's weight and size. The system can be configured such that the output of the processor can have a plurality of formats related to the predetermined posture modes (e.g. correct posture, hunching, slumping, leaning forward, leaning left or right, diagonal left or right, and slouching), and a user can select the format of the output. Moreover, the system can be configured to provide an alert when an operating condition of the system may affect the processor output in an undesirable way. Also, the system can be configured such that the output of the processor has at least one form that informs the user that the system is reacting correctly to the user's position on the seat component.

When the principles of the present invention are used in an ergonomic chair the user can be notified of the user's sitting position via a graphical desktop computer display (FIG. 1). The display can aid the user by offering a reminder of sitting position so that the user can make the necessary adjustments to ensure better posture. By giving posture feedback to the user, an ergonomic chair incorporating the principles of the present invention will initiate corrective action, and possibly prevent unnecessary health problems. FIG. 10 schematically illustrates the functional operation of a system according to the principles of the present invention In the design of the system of the present invention, applicants have sought to address the following needs of users, with respect to sensing a user's posture mode when seated on a seat component:
- The system would sense a person sitting in the chair
- The system would normally have limited weight capacity
- The system is designed for a low manufacturing cost
- The system preferably has wireless interface capability
- The system preferably has a graphical user display
- The seat component provides lumbar support
- The system is capable of being incorporated in a high back chair
- The system is designed with a long lasting power supply
- The system has plug and play/CD install software
- The system is non-obtrusive
- The system is comfortable
- The system is designed to have operating system compatibility with several known operating systems
- The system casing is small and relatively hidden

I. The Following Specifications Relate to an Original Prototype Chair Designed According to the Principles of the Present Invention (This is One Original Example, but the Principles of the Present Invention can be Practiced with a Broader Range of Specifications and Structure)

2.1 concept of Operation (e.g. FIGS. 1, 10)

2.1.1 System Modes

Power Off

When not in use the system will be shut down to conserve power.

Initialization

When powered on the system will go through an initialization to determine the user and their respective attributes.

System Active

When running the system will be collecting data from the sensing system and transmitting that data to the computer. The computer will then have two modes related to conveying this information to the user.

Passive Mode

In passive mode the system will record the data in the background, and allow the user to access this information at any time. The system will not alert the user of bad posture in this mode.

Active Mode

In active mode the system will record the user's position over time, and will alert the user when their posture could be harmful to their physical health.

Test Mode

In test mode the system will provide real-time feedback and give detailed output to help validate the system and to troubleshoot problems.

2.1.2 Description of System Deployment

The ergonomic chair 102 with active feedback has the main function of sensing the posture of a seated person and conveying this information to a personal computer. More specifically, the system will have four sub-functions as illustrated in FIG. 1. The four main sub-functions are: a sensing subsystem 101 for sensing a person, providing continual power to the sensing system and wireless interface 109 (via a power subsystem shown in FIG. 12 and a power flow chart shown in FIG. 11), interfacing with the computer, and conveying information to the user (via the feedback software subsystem 113), These subsystems were created to solve different functions that the system is designed perform. In order to see the correlation between the subsystems and the functions a chart was created, which is shown in chart 1 below. As seen in this chart each of the subsystems have one or more functions which it has to accomplish.

CHART 1

Subsystem to Sub-function mapping

| | | Power | Wireless System | Sensing System | | Computer System | |
|---|---|---|---|---|---|---|---|
| | | System Battery | Wireless Interface | Sensors | A/D Converter | Data Analysis | Graphical User Interface |
| Sense Person Sitting in Chair | Sense Pressure at Sensing Points | | | X | | | |
| | Convert Analog Pressure Signal to Digital Signal | | | | X | | |
| Interface with Computer | Collect Digital Pressure Data | | X | | | | |
| | Transmit Data to Computer | | X | | | | |
| Convey Information | Interpret Data to Determine Posture | | | | | X | |
| | Display Graphical Representation of Posture | | | | | | X |
| Provide Continual Power | Supply Power | X | | | | | |

2.2 Performance

The following section outlines the performance metrics of the system, which covers the sensing system, software, wireless data transfer, power supply, and the chair itself. Chart 2 below summarizes those performance metrics.

CHART 2

Performance Specifications

| Criteria | Specification |
|---|---|
| 2.2.1 Sensing System | |
|   2.2.1.1 Pressure Sensors | |
|     2.2.1.1.1 Range(psi) | 0-150 psi |
|     2.2.1.1.2 Durability(time compressed) | >10,000 hours |
|     2.2.1.1.3 Sensitivity | +/−0.15 psi |
|   2.2.1.2 A/D Converter | |
|     2.2.1.2.1 Speed | <15 µs |
|     2.2.1.2.2 Channels | 8-12 |
|     2.2.1.2.3 Precision (Output bits) | 8-12 |
|     2.2.1.2.4 Voltage Requirements | 2-5 V |
|     2.2.1.2.5 Current Requirements | <1 mAh/day |
| 2.2.2 Software | |
|   2.2.2.1 Data Collection/Analysis | |
|     2.2.2.1.1 Input Sampling Rate | 1/min-60/min |
|     2.2.2.1.2 Analysis time | <30 sec |
|   2.2.2.2 Graphical User Interface | |
|     2.2.2.2.1 Look and Feel | Windows-Like |
|     2.2.2.2.2 Output | Real-time/Graphs/Pictures |
|     2.2.2.2.3 Notifications | Audible/Pop-Up |
|     2.2.2.2.4 Accuracy | >=95% |
| 2.2.3 Wireless Data Transfer | |
|   2.2.3.1 Transmission Rate | 10 to 17 seconds random |
|   2.2.3.2 Current Requirement | <1 mAh/day |
|   2.2.3.3 Transmission Range | 10 to 20 feet |
|   2.2.3.4 Input Voltage | 0 to 10 Vdc |
|   2.2.3.5 Operating Temperature | −40 C. to 85 C. |
| 2.2.4 Power Supply | |
|   2.2.4.1 Voltage Requirements | 5-10 V |
|   2.2.4.2 Amp-Hour Requirements | 800-3000 mAh |
|   2.2.4.3 Battery Life | >1 month |
| 2.2.5 Chair | |
|   2.2.5.1 Weight Capacity | 95-300 lb |
|   2.2.5.2 Ergonomic Support | Use passively ergonomic chair |
| 2.2.6 Cost | |
|   2.2.6.1 Design and Development Cost | <$2000 |
|   2.2.6.2 Retail cost | <$100 |

2.2.1 Sensing System 2.2.1.1 Pressure Sensors 106

2.2.1.1.1 Range:

The pressure range the sensors will need to sense will be 0-150 psi.

2.2.1.1.2 Durability

The pressure sensors will be compressed during the entire time the chair is being used. Assuming an 8 hour work day for 5 days a week for five years, the sensors will need to last for at least 10,000 hours, 2.2.1.1.3 Sensitivity The sensitivity needed will give a resolution of less than 0.15 psi.

2.2.1.2 Analog to Digital Converter and multiplexer 107 (provided in a printed circuit board 130 shown schematically in FIG. 12)

2.2.1.2.1 Speed

Speed will be less than 15 µs.

2.2.1.2.2 Channels

The number of channels will equal the number of sensors: 8-12.

2.2.1.2.3 Precision

The number of output bits determines the precision. Precision needed will depend on the smallest magnitude of pressure change the system will need to detect.

2.2.1.2.4 Voltage Requirements
The voltage requirements need to be small to accommodate a long lasting power supply: 2-5V.
2.2.1.2.5 Current Requirements
The current requirements will be less than 1 mAh per day.
2.2.2 Software (Controlling Operation of the Processor 108)
2.2.2.1 Data Collection/Analysis
2.2.2.1.1 Input Sampling Rate
The input sampling rate will depend on how often the pressure sensors 106 will need to be read in order to have a good indication of sitting position. This will be anywhere from once per minute to once per second.
2.2.2.1.2 Analysis Time
The time required to analyze the data from the sensors needs to be kept under thirty seconds to make the feedback meaningful in real-time.
2.2.2.2 Graphical User Interface (Forming Part of the Feedback Software Subsystem 113)
2.2.2.2.1 Look and Feel
The user interface is a windows-like application that only requires mouse action and some text entry during calibration.
2.2.2.2.2 Output
The output contains graphs and figures that represent a person sitting in a chair. The output also is representative of current sitting position as well as monitor sitting position over time.
2.2.2.2.3 Notifications
The user interface (e.g. shown at 115 in FIG. 1) will have audible and/or popup notifications regarding bad posture and power supply.
2.2.2.2.4 Accuracy
The position monitoring ability of the software is designed such that the conveyed position on the GUI is correct at least 95% of the time.
2.2.3 Wireless Data Transfer (e.g. Via Wireless Interface 109)
2.2.3.3 Transmission Rate
The rate at which transmission will send data to the receiver shall be 1 second to 2 minutes.
2.2.3.2 Current Requirement
The current requirement for the wireless subsystem shall be no more than 1 mAh/day.
2.2.3.3 Transmission Range
The range of transmission from the receiver and transmission component shall be between ten to twenty feet.
2.2.3.4 Input Voltage
The input voltage shall be between 0 to 10 Volts.
2.2.3.5 Operating Temperature
The operating temperature shall be between −40° F. to 95° F. for normal operation.
2.2.4 Power Supply (see FIGS. 11 and 12)
2.2.4.1 Voltage Requirements
The power supply will need to provide 5 to 10 volts in order to power the A/D converter, sensors, and wireless component.
2.2.4.2 Amp-Hour Requirements
The amp-hours needed to power the sensing unit and wireless interface will be anywhere from 800-3000 mAh.
2.2.4.3 Battery Life
The power supply will need to last at least one month before needing a replacement battery.
2.2.5 Chair 102
2.2.5.1 Weight Capacity
The chair must be able to continually support a person weighing between 95 and 300 pounds.
2.2.5.2 Ergonomic Support
The chair must have good lumbar support and promote good posture.
2.2.6 Cost
2.2.6.1 Design and Development Cost
2.2.6.2 Retail Cost
The system is designed such that the production cost will be low enough to allow the chair to be sold for less than $100.

II. Brief Overview of Original Prototype Design

The Ergonomic Chair with Active Feedback is a system that detects a person's sitting posture and displays that posture on a computer screen. The basic design starts with a standard office chair. A sensor structure with pressure sensors 106 are is provided under the foam (between a seat cushion and seat frame portion) and signals from the pressure sensors are fed to a microcontroller (on the printed circuit board 130) that converts their analog signals to digital. This data is sampled via a multiplexer 107 and transmitted to a computer via a wireless or serial interface 109. Once the data is collected, it is analyzed to determine posture and is finally displayed in three different graphical views. This functionality is accomplished by the interaction of several subsystems.

1. The Chair Subsystem consists of the chair 102 itself and the casing 140 which holds the Electrical and Sensing Subsystems.

2. The Sensor structure 101 comprises the pressure sensors 106, the deformable pucks 114, 117, the flexible sheets 121, 123 with the pressure sensing pads 106a and the wiring embedded in the flexible sheets, which sensor structure is connected between the chair cushion and the chair frame.

3. The Electrical Subsystem is the circuitry to which the sensors are connected. It consists of an OP-AMP amplifier for each sensor (see FIG. 13) and an analog to digital converter microcontroller (that includes a multiplexer 107 (FIG. 1, Exhibit A) that controls the sampling of the sensors 106). The microcontroller, referred to herein as PIC (see paragraph 00155) also contains the components of the power subsystem (shown in FIGS. 11 and 12).

4. The Power Subsystem is composed of three different voltage regulators and a battery pack that provide portable power to the system (FIGS. 11 and 12).

5. The Wireless Subsystem 109 is comprised of a PROMI-ESD-02 Bluetooth embedded wireless module and a Bluetooth USB dongle.

6. The Data Collection and Analysis (DCA) Subsystem 113 is the software on the computer that collects and analyzes the data coming from the electrical subsystem to determine the posture.

7. The Graphical User Interface (GUI) Subsystem 115 displays the posture and allows the user to customize the system to them self.

III. Detailed Description of Prototype Subsystems 4.1 Chair Subsystem
4.1.1 Design
An exemplary example of chair 102 is an Executive Fabric Office Chair made by Novimex Fashion Ltd. Before assembling the chair, the chair back and bottom can be re-upholstered, to remove the foam padding from the wooden backing, upholster the foam and the wood pieces separately from each other, then use Velcro straps to secure the foam pieces to the wooden backing and allow the foam pieces to be removed from the chair quickly and easily. This setup is useful for both testing and display purposes.

The casing assembly 140 (FIG. 12) is responsible for physically constraining all of the electrical hardware components to the chair in a conveniently accessible yet non-intrusive fashion. The components forming the casing assembly 140 comprise a casing 128 and several components contained in the casing, including a Printed Circuit Board 130, a Power Switch 131, a Serial/Wireless Transmission Mode Switch 136, a db25 port 134, the serial port 132, and a Battery Pack 138. All of the above components except the Printed Circuit Board 130 are off-the-shelf parts that can be purchased (e.g. at Elliott Electronic Supply (1251 S. Tyndall Ave., Tucson, Ariz. 85713). To configure the components in a logical manner, the Power Switch 131 is situated on the side of the casing that faces the side of the chair to make it easily accessible to the user. The Battery Pack 138 is located on the bottom of the casing, allowing a hinged door and latch system to be fashioned for casing, to allow access to the user in the event that the batteries need to be replaced. The db25 port 134 is situated on the back side of the casing 128 to allow the wire ribbons from the chair bottom and back to plug into the port easily. The Serial Port 132 is located on the same side of the casing as the Power Switch 131, so that if a serial cord is used, it is easy to plug in and will not get in the way of the user's legs when sitting in the chair. The Transmission Mode switch 136 is located on the same side as the db25 port so that, although it will not be used as frequently as some of the other components, it is still somewhat accessible when needed. As for the Printed Circuit Board 130, it is positioned high enough in the casing to allow room for the Battery Pack and Power Switch below it, but far enough from the top to allow adequate cooling in case the Circuit. Board were ever in danger of overheating. In a production version of the casing, the casing is cast with flanges on the top to allow the casing to be bolted to the chair.

4.1.2 Exemplary Prototype

The assembly of a prototype chair required very little beyond following the assembly instructions included with the chair. However, the four bolts used to secure the legs to the chair bottom were too long and protruded through the wooden frame. They were cut down to length using a Wizard Rotary tool with a cutting disc attachment, and the tips of the bolts were painted to avoid corrosion at the exposed metal on the cut surfaces.

The casing 128 of the assembly 140 is made of ABS Plastic, which was chosen for its combination of low density, low cost, and good mechanical properties. To implement the design, an extended milling operation was performed on a block of ABS plastic to remove all the inner material and produce all of the desired geometry on the part. A drill press was used to make all the holes, and the holes for the Printed Circuit Board were tapped by hand. To finish the holes and obtain square corners, files were used in some holes to remove extra material. To fashion the battery door, a band saw was used to cut a thin section of ABS from a second block of the material, and a drill press was used to make holes for a brass hinge that was purchased at Lowes Hardware Store. A nylon wing nut was used as the latch for the battery door.

4.1.3 Testing

The only testing that was performed on the casing was a visual inspection of the fit of all components to be housed by the casing. All of the parts were installed in the casing, and they all fit correctly with no interference from other components.

4.1.4 Analysis

There was no significant analysis performed on the chair itself.

4.2 Sensing Subsystem 101

4.2.1 Design

The pressure sensors that applicants used in their prototype are the FlexiForce A201 pressure sensors manufactured by Tekscan (and shown in U.S. Pat. No. 6,272,936, which is incorporated by reference herein). The FlexiForce A201 force sensor is an ultra-thin, flexible printed circuit. The force sensors are constructed of two layers of substrate (polyester/polyimide) film. On each layer, a conductive material (silver) is applied, followed by a layer of pressure-sensitive ink. Adhesive is then used to laminate the two layers of substrate together to form the force sensor. The active sensing area is defined by the silver circle on top of the pressure-sensitive ink. Silver extends from the sensing area to the connectors at the other end of the sensor, forming the conductive leads. A201 sensors are terminated with male square pins, allowing them to be easily incorporated into a circuit. The two outer pins of the connector are active and the center pin is inactive.

The FlexiForce single element force sensor acts as a force sensing resistor in an electrical circuit. When the force sensor is unloaded, its resistance is very high. When a force is applied to the sensor, this resistance decreases. The resistance can be read by connecting a multimeter to the outer two pins, then applying a force to the sensing area. Chart 3 below describes the physical properties and the typical performance of the Flexiforce A201 Pressure Sensor.

CHART 3

Physical Properties and Typical Performance of Pressure Sensor

| | Flexiforce A201 Pressure Sensor |
|---|---|
| Physical Properties | |
| Thickness | 0.008" (.208 mm) |
| Length | 8" (203 mm) |
| Width | 0.55" (14 mm) |
| Sensing Area | 0.375" diameter (9.53 mm) |
| Connector | 3-pin male square pin |
| Thickness | 0.008" (.208 mm) |
| Typical Performance | |
| Linearity Error | <+/−5% |
| Repeatability | <+/−2.5% of full scale (conditioned sensor, 80% force applied) |
| Hysteresis | <4.5% of full scale (conditioned sensor, 80% force applied) |
| Drift | <3% per logarithmic time scale (constant load of 90% sensor rating) |
| Response Time | <5 microseconds |
| Operating Temperatures | 15° F. to 140° F. (−9° C. to 60° C.) |
| Force Ranges | 0-25 lbs. (110 N) |
| Temperature Sensitivity | Output variance up to 0.2% per degree F. (approximately 0.36% per degree C.) |

The pressure sensors that were used are ultra-thin, accurate, simple to use and cost-effective. The fact that it is only 0.208 mm thick makes it non-obtrusive to users, and therefore fulfills one of the objectives of the sensors in a system of the present invention.

Since the output of the of the sensors is a measure of resistance, the sensor is incorporated into an operating amplifier (op-amp) circuit so as to obtain a voltage output, which will then be fed as the input to the PIC, since the latter typically takes voltage as its input. The 0-25lb. Flexiforce sensor is incorporated into a non-inverting op-amp configuration. The sensor itself acts as a variable resistor and provides a negative feedback when connected in a non-inverting configuration. There are many advantages in using the negative feedback path, namely, it helps to overcome distortion and nonlinearity, it makes the output predictable, less dependent on temperature, manufacturing differences or other internal properties of the active device and circuit properties are dependent upon the external feedback network and are thus easily controlled by external circuit elements. The operational amplifier used is the well-known LM741CN manufactured by National Semiconductor. Since the gain is given by (Rsensor/R1)+1, R1 is set to be 320 k$\Omega$ to maximize gain and at the same time sustain output linearity. A large resistor, in this case, 500 k$\Omega$ is used as R2 to minimize the amount of current going into the non-inverting input, in order to emulate the ideal op-amp behavior.

4.2.2 Prototype

For this prototype, each sensor is incorporated into the non-inverting op-amp configuration. Since the voltage is read from each op-amp, this results in 22 pieces of 24 AWG single core wires soldered onto the PCB, where the other end of the wire is connected to a female-to-female header via a heat shrinking plastic tube. The other end of the female header is connected to a ribbon-to-female connector. A male-to-male DB25 serial connector is then used to connect to female connectors on both sides. The ribbon part of the second ribbon-to-female connector connects to the sensor male square pins via heat shrinking plastic tubes. Heat shrinking plastic tubes and crimps were used instead of soldering in order to reduce the possibility of disconnected wires.

In determining sensor locations, based upon intuition from watching different people sit in chairs, sensors were placed on the seat bottom in a systematic order and performed data collection on 9 sitting positions. This was experimented on five subjects, three men and two women. Based upon that, graphs were generated to represent the magnitude of each sensor in relation to the upright position. The patterns on certain sensor locations were observed from the graphs. The same procedure was performed on the seat back. After observing the pattern behavior on the graphs, sensor locations were chosen based on their ability to detect the major posture modes—upright, left, right, slouch, hunch, and lean forward.

Design of Experiment (DOE) was then used to further improve the sensor locations so that the major posture modes can be detected more accurately. A test matrix was constructed to analyze the different values that were generated through different sitting positions. These values correspond directly to the difference between the value generated from a certain sitting position and its normalized value.

Also, in order to increase the sensitivity of pressure sensing, round aluminum pucks were attached to the round sensing area using double-sided tape.

4.2.3 Testing

The circuit shown on FIG. 13 was built and tested for its output. Instead of using the sensor as Rsensor, a potentiometer was used instead to emulate the sensor, since the latter behaves as a variable resistor. This method was employed because it was easier to adjust the resistance from a potentiometer rather than applying unknown forces on the sensor to vary its resistance.

4.2.4 Analysis

After testing the circuit built as shown in FIG. 13, it was observed that the output voltage decreases steadily as the resistance of the potentiometer decreases. After running a simulation on PSpice based on the circuit shown on FIG. 13, R1 and R2 are determined to be 320 k$\Omega$ and 500 k$\Omega$ respectively. By using these resistor values, the output voltage is linearly proportional to the changing resistance of the sensor. FIG. 14 shows the plot of the output voltage vs. the resistance of the sensor, as simulated on PSpice. The resistance of the sensor ranges from 220 k$\Omega$ to 1 M$\Omega$.

Since a higher resistance corresponds to a lower force, therefore a higher output voltage corresponds to a lower force applied. The rail voltage of the operational amplifier is set to 4-5V, so that the output can swing within the vicinity of 0-5V. The +5V is supplied from the PIC, thus eliminating the use of external power sources.

4.3 Electrical Subsystem

The Electrical Subsystem provides most of the functionality of the non-software side of the overall system. It is comprised of the microcontroller provided on the printed circuit board 130 that organizes and controls the flow of data as well as provide analog to digital conversion for the sensor signals, the opamps that allow for a buffer between the sensors and the microcontroller, and the embedded side of the serial and wireless interfaces.

4.3.1. Design

After choosing the sensors, applicants determined that they needed to turn a changing resistance into something that computer software can use. This would have to involve an analog to digital (A/D) conversion. Since applicants were estimating the use of twelve sensors, applicants needed a microcontroller with at least twelve A/D input channels. Applicants also needed to be able to transmit the information from the chair to the computer either serially or wirelessly. Thus, applicants needed a microcontroller that could communicate in this way. After searching, the PIC18F4320 (referred to herein as PIC) was selected as the microcontroller. It is a 16 bit microcontroller with a serial interface as well as 13 A/D input channels with 10 bit precision.

4.3.1.1 Analog to Digital Conversion

The analog input to the PIC needed to have a low input impedance. This was accomplished by the use of operational amplifiers (op-amp) in a non-inverting amplifier configuration using the sensor as the feedback resistor. (FIG. 13 in Sensing Subsystem) This allowed for the changing resistance of the sensor to cause a changing voltage on the A/D inputs. Each op-amp is also powered by the PIC one at a time in order to reduce the constant current drain.

4.3.1.2 Serial Interface

The PIC has a USART serial interface that uses the TX and RX to transmit and receive data in 8 bit increments. Because of the difference in voltage between the PIC and a desktop computer's serial port, the MAX232 line driver was used to change the voltage levels. The MAX232 is an industry standard.

4.3.1.3 Wireless Interface

The PIC also needed to communicate with the embedded wireless module (PROMI) which operated with 3.3V. This was accomplished by using a voltage divider for the input to PROMI and a double common-emitter transistor configuration to boost the output of the PROMI to 5V. The level shifter can be seen in Figure 4.3.1.

A three connection/three position switch was used to toggle between serial and wireless use. The switch connects the power, TX, and RX for the desired interface and isolates the other. This reduces current drain by having only one interface powered at a time and is also necessary to prevent signal tampering that is caused when both are connected at the same time.

4.3.2 Prototyping

4.3.2.1. Construction

Originally, the first circuit was built on a breadboard in order to be adjustable for testing. The final circuit was put on a PCB that was designed using the free software www.ExpressPCB.com and ordered through the same company. The circuit board is a two layer 4.5"×4.5" standard PCB. It holds all of the opamps, voltage regulators, microcontroller, serial, and wireless modules. It has connections available for the external components such as the power switch, the RS232, the serial-to-wireless switch, and all of the incoming sensor leads. The schematics for all of the electronics and the PCB can be found in Exhibit. B. Exhibit B comprises three figures that show the schematics and board layout for the chair electronics assembly: The figure that is page 3 of Exhibit B shows the individual op amp circuits connected to each pressure sensor. Each sensor is shown as SX, where X is a value from 0-10. This op-amp feedback configuration provides a voltage output that is primarily dependent on the resistance of the pressure sensor. Each pressure sensor's resistance is a function of the current load on the sensor. The embedded computer and wireless systems are shown in the figure that is at page 2 of Exhibit B. The PIC processor in the upper left of the figure both receives the analog voltage associated with each sensor's pressure load, but also controls the op amp supply voltage. This latter function allows the op amps to be shut off between measurements and conserves power. The other key function of the PIC is to communicate with the communications system (upper right). The PRx and PTx signal represent the receive and transmit communications, respectively. The communications system can send out data via an RS-232 port (via wire for diagnostic purposes) or through the PROMI-ESD-02 part for wireless communications. The remaining schematics on the bottom of the figure represent the battery and the various voltage regulators in the system. The figure labeled that is at page 1 of Exhibit B shows the board layout used to implement the schematic diagrams.

4.3.2.2 Programming

Programming of the PLC was done with free software, MPLAB IDE, which can be found on www.microchip.com, and which was used to program and simulate the PIC using the C programming language. The basic operation of the PIC is to work in an infinite loop of sleeping and transmitting. The PIC is usually in sleep mode waiting for an input from the serial port. The RX of the serial input is tied to the INT0 interrupt pin. Any time a signal comes in, the PIC wakes up and begins its cycle through each sensor. For each sensor, the PIC first powers up the corresponding opamp, then it enables the specific analog input channel, then it waits the required acquisition time, finally it samples the voltage level and starts the conversion. Once the conversion is done, it transmits the data collected. Since the data is 10 bits and only 8 bits can be transferred at a time, it must be divided into two transmits. The first of three transmissions per sensor is the sensor number, followed by bits 7-0, and finally bits 9-8. Once the transmission of each sensor is complete, the PIC goes back into sleep mode to await the next request. The code can be found in the attached disc.

4.3.3 Testing and Analysis

The first testing performed was regarding the serial interface. It was important to establish the correct BAUD rate for transmission. After trying several configurations, the 2400 BAUD rate turned out to be the most reliable.

After the BAUD rate was determined, testing of the A/D conversion was performed. A fixed voltage was established on one of the analog inputs and a conversion was induced and the data was transferred as discussed. Because the data sent was in integer form, it had to be converted first to a ten bit binary number, and then into the actual voltage value. Initial tests showed the accuracy of the analog to digital conversion to be within 0.005V.

Once it was determined the analog to digital conversion worked, the sleep mode was tested and was successful.

Finally, the cycling through of the sensors was tested and was successful.

Once all of the testing for the analog to digital conversion and serial interface was complete, our attention was turned to making the wireless interface work. This proved to be the most difficult as it was initially difficult to configure the wireless device, and then it was unknown at first that the voltage levels needed to be shifted. Once this was figured out, the wireless worked perfectly and the electrical subsystem was complete.

4.5 Power Subsystem

4.4.1 Design

Four AA batteries will be used to power the system. Since the microcontroller and the Bluetooth Wireless will require 5V and 3.3V respectively, a voltage regulator shall be utilized to provide the required voltages.

The ADP667 manufactured by Analog Devices is the choice voltage regulator to supply +5V. This particular chip is designed to output +5V without the usage of external components. The circuit for this is shown in FIG. 13.

The UCC283-3 positive linear voltage regulator manufactured by Texas Instruments is used to provide a +3.3V input to the PIC microcontroller. This chip is constructed as a simple 3-lead package, with a built-in reverse voltage sensing that prevents current in the reverse direction. The quiescent current is always less than 650 µA, making it ideal for low-power applications.

4.4.3 Testing

The sensor 106, which is incorporated into a non-inverting operational amplifier configuration, uses a +1.8V input voltage and a +5V rail voltage, where the latter limits the output voltage range to swing from 0-5V. Since 11 operational amplifiers are used in this application, each gets its +5V rail voltage from one pin of the microcontroller, thus eliminating the use of additional power supply. As for the input voltage, the TLV2217-18 voltage regulator manufactured by Texas Instruments is used to provide +1.8V to the operational amplifier. This chip provides convenient features that include internal over-current limiting, thermal-overload protection, and over-voltage protection. Similar to the +3.3V regulator, the +1.8V regulator is constructed as a simple 3-lead package.

4.4.4 Analysis

For the prototype, applicants used four AA batteries, which have a capacity of approximately 2850 mAh. With the wireless module incorporated, applicants measured the current coming from the batteries, where 30 mA was recorded. The battery lifetime is calculated by taking the ratio between the capacity of the batteries and the amount of current drain. Taking into account only the operating mode, the battery lifetime is calculated to be approximately 100 hours.

4.5 Wireless Subsystem

4.5.1 Design

The Bluetooth wireless module was selected, because it allowed short-range, low-power wireless transmission. Bluetooth technology is also becoming more common in applications and new desktop systems. Finally the Bluetooth hardware allowed for serial communication, which meant the programming for the PIC would not have to change from the serial cable communication to the wireless communication. The Bluetooth module originally designed around did not have the information needed for implementation, thus the Promi-ESD-02 was used. This chip came with a development board and software to setup the baud rate and handshaking parameters first used. Being, that the baud rate for the PIC was 2400 bps, the Bluetooth device needed to be set to this as well in order to ensure seamless integration.

When first attempting to implement this wireless chip there were a number of issues encountered. First, when seating the chip into the development board for programming there was a connection error, and half of the time the program could not connect to the chip. In order to solve this problem all of the leads on the development board were wired to a corresponding spot on an adjacent bread board. Once connecting the chip through this configuration there were no more connection errors. The next issue the wireless had was a wiring problem. The original PCB had the TX and RX switched, which would not allow any data transmission to occur. Once this problem was figured out and resolved, a connection and data flow was established.

After this was solved there was an issue with the repeatability of the wireless connection. The connection would work the first time after it was programmed, but failed to transmit data thereafter. In order to solve this issue a number of things were changed. To begin with the "Signal" setting on the device had to be switched off. Also on the chairs circuit board, the CTS pin had to be tied to ground, and the RST pin had to be tied to Vdd.

After solving these connection issues a new issue surfaced. The connection became very finicky, and after further analysis it appeared that, the output voltage from the TX pin was well below the 5 v that the PIC required. This was a combination of the 3.3 v that the wireless device ran off of, and an apparent voltage drain from the serial port still being tied to the TX line. In order to solve this problem in the second PCB design a switch was created that had the capability to not only power either the serial or wireless, but isolate their connection to the PIC's TX and RX pins.

In order to ensure that the wireless connection was working correctly the system had to connect from the Promi-ESD-02 to the standard Bluetooth device on the computer side of things. The standard device being used for this system is a DUNK USB dongle DBT-120.

To initiate the connection the Promi was set to standby for connection and the DUNK searched for available devices and paired with the Promi. The Promi security code was set to 3333 in order to ensure this closed loop system was the only one connected to the chair at this time. Before the sensors were connected correctly the com port was opened using HyperTerminal to test the connection. At this point the "Signal" setting had to be turned on to allow the chip to respond to AT commands. After some trouble connecting everything worked and the system responded to the AT commands. Once the sensor circuits were all working correctly the wireless was opened using the Java terminal program. The program is set to open the port and write and read serially to the port. The incoming data is then displayed on the screen. After overcoming the problems described above in connection with the wireless transmission, the wireless began to work without error.

4.5.4 Analysis

In order to ensure that the wireless was a feasible communication tool, the integrity of the data was analyzed. In order to do this there were a number of readings taken in the serial mode and the wireless mode. Both the no-load and loaded cases were tested, along with real-time output as each sensor had a certain force applied to it. The output of this testing was that the wireless system produced as accurate data as the serial chord communication. Also this testing showed that the sensors often took between one and two seconds to level out to display their actual current load.

4.6 Data. Collection and Analysis Subsystem 4.6.1 Design

The DCA subsystem is the first part of the software side of the whole system. It is responsible for the serial communication with the electrical subsystem and converting the data collected into meaningful values.

The Java software used for serial communication was borrowed from the SerialDemo classes provided by the Java Communications API. Some of the classes were modified to better pertain to the purposes of the project. Modifications are clearly commented in the code.

Once the serial communication part was working, the incoming data needed to be manipulated. The data coming in was in three bytes representing different parts of the 10 bit digital voltage value. The integers read from the serial port were first split into an actual 10 bit binary number, represented by an array of 1's and 0's. After this was complete, the correct value for each bit was added to get an actual voltage reading. Bit 9 represents 2.5V, and each subsequent bit represents a value of half that of the previous bit. Thus, an array of all 1's is equal to 5V.

Because the voltage levels coming from the PIC are inversely proportional to pressure, a further manipulation was used to flip that proportionality. Due to the precision of 0.005 volts, each value was multiplied by 1000 and subtracted from 5000. This returns a value that is a maximum of 5000 and representative of pressure at that sensor. These values were used for all subsequent data collection and analysis.

Finally, the analysis part of this subsystem also includes the posture mode determination algorithm. This algorithm computes a series of sums for the different areas of the chair, such as the right and left side, the bottom and back, and the front and rear. Furthermore, these sums are also compared to the sums computed from the upright calibration. The final decision is made through a series of 'if' statements regarding how each area of the chair compares to other areas.

4.6.2 Prototyping

Prototyping only consisted of writing the code and compiling it.

4.6.3 Testing

Once the serial communication and data manipulation part was complete, much data was collected for several different people sitting in nine predetermined sitting positions. Each set of data would be compiled into spreadsheets that would depict graphically what the weight of each sensor was.

4.6.4 Analysis

Data analysis was approached in a graphical context using visual comparisons to decide on algorithms and sensor placement.

4.7 Graphical User Interface Subsystem 4.7.1 Design

The GUI subsystem is the controlling interface between the human user and the rest if the system. The GUI has several buttons that will allow the user to adjust the system. The buttons consist of a button that takes a no load reading, a button that calibrates the system to the human user's upright posture, a button that will start the connection and just start taking data, a button for displaying the posture view, a button that shows the posture versus time and finally a button that shows the sensors and their locations in the chair.

4.7.1.1 No Load Calibration Button

This button should be pressed when the person is standing. It allows the system to take a reading of the chair while no one is sitting in it. This allows for a good sensor check of the readings the sensors may be giving out.

4.7.1.2 Upright Calibration Button

Tailor's the system to a new user of the chair. The sensors will take some readings from the human user and then calibrate the chair to the new person sitting in the chair.

4.7.1.3 Start Connection Button

Begins the feed of information from the sensors. The sensors will send the data to the software and a posture mode is calculated.

Based on this posture mode a picture of the current sitting position will be displayed.

4.7.1.4 Posture View Button

Displays user's posture using pictures in the main panel.

4.7.1.5 Posture Versus Time Button

Displays a graph of the current posture versus time.

4.7.1.6 Sensor Display Button

Displays a layout of the sensors located in the chair and the effects of pressure on the sensors.

4.7.2 Prototyping

During the prototyping of the software there were a number of changes that were made on the fly. To begin with the original software was done in c++. While everything appeared to be heading in the correct direction as the graphical user interface began to work and the serial port class began to work, it was all inhibited by the failure of the wireless class. The virtual serial port which c++ sets up for the Bluetooth dongle was corrupting the data as a result of the event driven format. Through extensive attempts to solve this problem the decision was finally made to switch over to the functioning Java code.

The Java code being used at that point was successfully communicating wirelessly and serially, and could also manipulate the data coming in. In order to implement this code another GUI was created, along with the posture classification algorithm. This code was then modified to the final version used in the presentation.

4.7.3 Testing

Extensive testing and data analysis was completed at the beginning of the Java data flow completion. Numerous readings were taken for a number of different users, and then compared to one another to ensure the data collection was working correctly, and to help devise the algorithm for posture classification. Once the readings became fairly constant the algorithm was created and tweaked to work around the average user which is about 5'10" 180 lbs. This divides our sample in half being that the system has to work for the 95 lb person to the 300 lb. person. After the algorithm was functioning correctly for this user, and various users around this size, other users were then introduced to the system. A wide variety of users were tested with this configuration, and slight changes were made in order to account for the variability of the user's size.

4.7.4 Analysis

The analysis of the results took place in the early stages of the software development. The output of the data brought in by the software was graphed and manipulated in Excel to calculate the variance and standard deviation of the sensors and readings. From this the wireless and serial were both verified, and the sensor location was selected. The analysis of the posture classification class took place through extensive testing and various users. The conclusion based on in-depth testing was that a more complex algorithm is needed for future development of this product. The current setup allows the system to classify the posture modes with a large amount of accuracy for those people larger in size. The algorithm begins to break down for smaller people, especially females in the case where they sit with their legs together. With the current sensor placement and the accuracy of the algorithm it is difficult to distinguish which direction they are leaning, because all of their weight is focused in the middle of the chair regardless of their direction.

IV. Detailed Description of Entire Prototype Design

5.1 Sensor Implementation

To house the sensors within the chair, a special sheet of Polyethylene plastic was fashioned. First, two sheets of Polyethylene were cut to just larger than the dimensions of the chair bottom to form the bottom sheet pair 123. Then, the sensors were placed in their final locations on one of the sheets using double-sided tape. The second sheet was placed over the first sheet so that the sensors were sandwiched between the two pieces of plastic. Then, using a standard laundry iron and two flat pieces of sheet metal, the Polyethylene sheets were bonded together around the entire outer edge. To do this, the plastic sheets were placed between the pieces of sheet metal, and the hot iron was placed on top of one of the pieces of sheet metal. Hand pressure was applied to the iron for 30 seconds to squeeze the plastic together and force heat to pass through the sheets until they had bonded together. Then, the iron was removed and a standard Barbell weight plate was placed on top of the sheet metal to pull the heat away from the plastic sheets quickly. The weight plate was left in place for approximately two minutes, after which the plastic sheet was carefully peeled away from the sheet metal pieces and inspected for proper bonding. This process was repeated to bond the entire border of the chair bottom sensor sheet in roughly four inch sections, and the whole thing was repeated again for the chair back sensor sheet pair 121.

Once the sensors were housed in two pairs of plastic sheets (one pair 121 for the chair back and one pair 123 for the chair bottom), they needed to be assembled into the chair itself. Thick strips of adhesive-backed Velcro 110 were applied to the wooden frame pieces of both the chair back and bottom, and the other sides of the Velcro strips were applied to the plastic sheets so that they lined up correctly. Then the sheets were pressed on to the chair so that the Velcro strips lined up properly, and the Velcro joints are what keep the sheets in place during use.

The wires coming from the sensors of a sheet pair were lead to a header (e.g. wire terminal 126 in FIG. 4) that was attached to a ribbon cable 122 (see also FIG. 7). The other end of the ribbon cable is attached to a female DB25. This DB25 was then attached to the other female DB25 which was wired to the PCB via a male-male DB25 gender changer. This allows the sensing sheets to be detachable from the casing unit.

5.2 Casing Implementation

To attach the casing assembly to the chair, Velcro strips were used. First, one side of the Velcro was stapled to the bottom of the chair in the desired location (see Appendix for an illustration of casing placement). Then, adhesive-backed Velcro strips were applied to the inner faces of the casing and allowed to drape over the top so that there was adequate surface area of the Velcro to bond with the pieces on the chair. Finally, the casing unit was positioned in place on the bottom of the chair and pressed into place.

5.3 Electrical Housing

The electrical subsystem is housed within the casing 128 (FIG. 12). The PCB 130 sits on the upper shelf with wires coming off of it that are connected to the power switch 131, serial-wireless switch 136, or serial port 132, which is an RS232. The circuit board 130 is accessible when the casing is taken off of the chair as there is an open top. The bottom half of the circuit board is also accessible by opening the battery hatch.

5.4 Software and Wireless

The software interacts with the wireless 109 by using a serial port program that speaks directly to a virtual con port assigned by the Bluetooth USB Dongle. When the software wants to take readings from the sensors it sends an arbitrary byte through the virtual com port to the Promi-ESD-02 device which is then sent to the PIC. The PIC will then gather data from the sensors and then send that data back through the Promi-ESD-02 device to the virtual com port assigned by the Bluetooth USB. The program then takes the data and does the necessary calculations to create a posture mode,

VI. Summary and Comments Regarding Original Prototype

6.1 Summary

The ergonomic chair with active feedback system has been completed and the posture modes have been classified. With the intent of proof of concept this project has completed the requirements and finished under budget. The design is manufacturable and can fit seamlessly into the chair manufacturing process. While this product is currently working as a proof of concept, there are a number of things that need to be addressed prior to the marketing and distribution of this product, as set forth below.

6.2 Comments

- Instead of using op-amps that have only one amplifier in a chip, use a quadruple amplifier chip. This would reduce the space needed on the PCB.
- The current sensor location was tested to be optimal for many posture modes, however it does not have a good account for people sitting with their legs together. Thus it is suggested that another two sensors be added to the middle right and middle left of the seat bottom. This will help to measure weight shifts for people of smaller stature and help account for this issue.
- The current posture classification algorithm works for larger people that can have a larger force impact on the sensors, but additional development is contemplated to ensure that all body types can be accounted for.
- While the system is able to classify the posture of its user, applicants contemplate developing some hard data when alerting the user of the user's "bad" posture.
- If using the .Net framework applicants suggest not use a serial port class to access the virtual com port, as the WaitingEvent function that is called in the serial port class may corrupt the data as it comes into the port.
- Another possible application to be considered for this product is use by paraplegics. Their inability to monitor their own posture and weight distribution often leads to blood clots and further health problems. This could be solved by monitoring where their weight is applied and for how long it is applied in these locations.

Thus, as seen from the foregoing description, the principles of the present invention were used to produce information about the posture of a user applying pressure to a seat component. A sensor structure comprising an array of sensors were connected with the seat component, at predetermined locations and in a predetermined pattern configured to provide output signals related to predetermined posture modes of the user applying pressure to the seat component. The output of the sensors was in circuit communication with a processor to provide signals to the processor related to predetermined posture modes of the user applying pressure to the seat component, and the processor provided output related to the predetermined posture modes of the user applying pressure to the seat component.

Moreover, in the system described above, the processor had an output that is in circuit communication with a posture mode indicator that provided an indication of the posture mode of the user applying pressure to the seat component. Also, the predetermined pattern of the sensors was designed to provide output related to any or all of the following posture modes: correct posture, hunch, slumping, leaning forward, leaning left or right, diagonal left or right, and slouching. Each sensor was formed as a pressure pad in force transmitting relation with a predetermined location on the seat component, each sensor configured to receive a load applied to the predetermined portion of the seat component such that the array of sensors provides output related to any or all of the following posture modes: correct posture, hunch, slumping, leaning forward, leaning left or right, diagonal left or right, and slouching. In a currently more preferred from, each sensor includes a force transmitting member connected to and extending between the pressure pad and a predetermined location on the seat component, the force transmitting member formed of elastically deformable material and configured to spread a load applied to the predetermined portion of the component and to transmit the load substantially across the pressure pad, such that the sensor provides output related to any or all of the following posture modes: correct posture, hunch, slumping, leaning forward, leaning left or right, diagonal left or right, and slouching. Also, the pressure pad of each sensor rests on one side of an elastically deformable support member and the other side of the elastically deformable support member is connected to a base member that is used to connect the sensor to a support.

Still further, in the preferred form of the present invention, the array of sensors is prepackaged in a sensor structure so it can be delivered to a user in the predetermined format. The array of sensors are connected to and disposed between a pair of flexible sheets, in a predetermined pattern, to form a preformed sensor array. At least one of the flexible sheets has sensor locating markings thereon, to enable the elastically deformable pucks to be attached to the flexible sheets, in predetermined force transmitting relationship to the sensors, during assembly of the preformed sensor structure. Additionally, at least one of the flexible sheets has a wire layout that enables the array of sensors to be connected to a terminal via the wire layout.

Moreover, in the currently preferred form of the system of the present invention, the seat component comprises a cushion and the sensor structure is connected between the cushion and a frame portion of a chair. Also, in the sensor structure, the array of sensors are located in a predetermined pattern in relation to the cushion, the predetermined pattern being designed such that the array of sensors will provide signals to the processor that are related to the predetermined pressure modes. In addition, the seat component comprises the seat, arm and/or back cushion of a chair, and the sensor structure is located between predetermined patterns in the seat, arm and/or back cushions and the relatively hard frame portions of the chair. Still further, it will be clear to those in the art that the layout of the sensors in the sensor structure can be modified to fit the geometry of different chairs.

Thus, the present invention provides a new and useful concept for producing information about the posture of a person applying pressure to a seat component. While the foregoing description relates to an exemplary system, in which information is provided via a computer, it is contemplated that other ways of providing the information can be used, in accordance with the principles of the present invention. For example, in a system that applicants refer to as a "stand alone" system, the posture mode analysis software may be provided in a processor that is embedded in the seat component, and a simplified user interface with a few buttons (controls) replaces the computer software controls. That interface may comprise, e.g. (a) an ON/OFF button, (b) a button that initiates a function verification check (e.g. a light emitting diode or small liquid crystal display readout), (c) a button that initiates a calibration, function, (d) a button that initiates a calibration check (e.g. via a buzzer, vibration, etc.), (e) an output (e.g. buzzer, vibration, etc.) that alerts a user of a bad posture, and (f) a device that gives a user an opportunity to set the bad posture alert time (e.g. dial or button choices). Such a stand-alone system is designed for uses in which a PC is not available or not desired. Some examples of such a situation are automobile and truck drivers, manufacturing-line and business workstations without PCs, or simply seating areas not associated with a PC (e.g., a reading area).

With the foregoing description in mind, the manner in which the principles of the present invention can be applied to various types of seat components will become apparent to those in the art.

The invention claimed is:

1. A system for producing information about the posture of a user applying pressure to a seat component that comprises a cushion supported on a frame member, comprising
a sensor structure, comprising an array of sensors connected with the seat component and supported on a flexible sheet that is located between the cushion and the frame member, at predetermined locations and in a predetermined pattern configured to provide output signals related to predetermined posture modes of the user applying pressure to the seat component, each sensor comprising a pressure pad and a pair of elastically deformable force transmitting members, one of which extends between the pressure pad and the cushion and the other of which extends between the pressure pad and the frame member, the pressure pads configured to spread a load applied to the predetermined portion of the component and to transmit the load substantially across the pressure pads;
the output of the sensors in circuit communication with a processor to provide signals to the processor related to predetermined posture modes of the user applying pressure to the seat component,
the processor providing output related to the predetermined posture modes of the user applying pressure to the seat component, and
wherein a flexible sheet is associated with the seat component and is located between the cushion and the frame member of the seat component, the flexible sheet having a plurality of flexible flaps, in a pattern such that the flexible flaps define the sensor locations, wherein the pressure pad and the elastically deformable force transmitting members of each sensor are located on a respective flexible flap of the flexible sheet.

2. A system as defined in claim 1, wherein the processor has an output that is in circuit communication with a posture mode indicator that provides an indication of the posture mode of the user applying pressure to the seat component.

3. A system as defined in claim 2, wherein the posture mode indicator comprises any or all of the following: a visual output, an audio output, a vibration output, or an output that is directed to a data file.

4. A system as defined in claim 3, wherein the posture mode indicator comprises a visual display that provides pictorial information that is related to the posture mode of a user applying pressure to the seat component.

5. A system as defined in claim 1, wherein the predetermined pattern of the sensors is designed to provide output related to any or all of the following posture modes: correct posture, hunch, slumping, leaning forward, leaning left or right, diagonal left or right, and slouching.

6. A system as defined in claim 1, further including a calibration mechanism that enables the system to be calibrated to a particular user's weight and size.

7. A system as defined in claim 1, wherein the predetermined pattern of the sensors is designed to provide output related to any or all of the following posture modes: correct posture, hunch, slumping, leaning forward, leaning left or right, diagonal left or right, and slouching.

8. A system as defined in claim 7, further including a calibration mechanism that enables the system to be calibrated to a particular user's weight and size.

* * * * *